United States Patent
Shirasawa et al.

(10) Patent No.: US 8,580,562 B2
(45) Date of Patent: Nov. 12, 2013

(54) INHIBITORY RNA FOR MODULATING THE MOLECULAR FUNCTION OF ZFAT GENE

(75) Inventors: Senji Shirasawa, Fukuoka (JP); Takahiro Fujimoto, Fukuoka (JP); Toshiyuki Tsunoda, Fukuoka (JP); Keiko Doi, Fukuoka (JP); Midori Koyanagi, Fukuoka (JP)

(73) Assignee: Fukuoka University, Fukouka-Shi (JP)

( * ) Notice: Subject to any disclaimer, the term of this patent is extended or adjusted under 35 U.S.C. 154(b) by 3 days.

(21) Appl. No.: 13/062,673

(22) PCT Filed: Sep. 8, 2008

(86) PCT No.: PCT/JP2008/066155
§ 371 (c)(1),
(2), (4) Date: May 24, 2011

(87) PCT Pub. No.: WO2010/026660
PCT Pub. Date: Mar. 11, 2010

(65) Prior Publication Data
US 2011/0237647 A1    Sep. 29, 2011

(51) Int. Cl.
C12N 15/85    (2006.01)
C12N 15/63    (2006.01)
C07H 21/02    (2006.01)
C07H 21/04    (2006.01)

(52) U.S. Cl.
USPC ....... 435/325; 536/23.1; 536/24.5; 435/320.1

(58) Field of Classification Search
None
See application file for complete search history.

(56) References Cited

PUBLICATIONS

Scherr et al. (Cell Cycle, 2003, vol. 2, Issue 3, pp. 251-257).*
"International Search Report, dated, Sep. 30, 2008, issued in PCT/JP2008/066155".
Kanno et al., "Jiko Men'eki Shikkan Kanjusei Idenshi Tagata ga Men'eki Kanren Idenshi no Hatsugen ni Ataeru Eikyo", Annual Meeting of the Japan Society of Human Genetics Program Shorokushu, 2007, vol. 52, pp. 162.
Kochi et al., "Kansetsu Rheumatism Kanren Idenshi no Dotei to sono Kino Kaiseki, Sogo Kanren no Kenkyu, Kansetsu Pheumatism Kanren Idenshi no Dotei to sono Kino Kaiseki, Sogo Kanren no Kenkyu", Heisei 19 Nendo Sokatsu Buntan Kenkyu Hokokusho, May 9, 2008, pp. 12-14.
Koyanagi et al., "ZFAT expression in B and T lymphocytes and identification of ZFAT-regulated genes", Genomics, May 2008, vol. 91, No. 5, pp. 451-457.
Nakabayashi et al., "Men'ekikei Tensha Kanren Inshi ZFAT no Tensha Network no Kaimei", Annual Meeting of the Japan Society of Human Genetics Program Shorokushu, 2007. vol. 52, pp. 118.
Fire et al., Nature, "Potent and specific genetic interference by double-stranded RNA in Caenorhabditis elegans", Feb. 19, 1998, vol. 391, pp. 806-811.
Elbashir et al., Nature, "Duplexes of 21-nucleotide RNAs mediate RNA interference in cultured mammalian cells", May 24, 2001, vol. 411, pp. 494-498.
Shirasawa et al., "SNPs in the promoter of a B cell-specific antisense transcript, SAS-ZFAT, determine susceptibility to autoimmune thyroid disease", Human Molecular Genetics, 2004, vol. 13. No. 19, pp. 2221-2231.
Shirasawa et al., "Jiko Men'ekisei Kojosen Shikkan Kanjusei Idenshi no Tansaku", Protein, Nucleic acid and Enzyme, 2005, vol. 50, No. 16, pp. 2097-2102.
Tochio et al., Structural and functional analyses of the ZFAT protein involved in auto-immune thyroid disease (AITD), Seikagaku, Shoroku CD, 2007, p. 4P-1079.
Ui-Tei et al.,"Sensitive assay of RNA interference in *Drosophila* and Chinese hamster cultured cells using firefly luciferase gene as target", FEBS Letters, 2000, vol. 479, pp. 79-82.

\* cited by examiner

*Primary Examiner* — Amy Bowman
(74) *Attorney, Agent, or Firm* — Birch, Stewart, Kolasch & Birch, LLP

(57) ABSTRACT

The inhibitory RNA for inhibiting the expression of ZFAT gene according to this invention is a siRNA comprising a sense RNA having a base sequence of contiguous 20 to 20 bases, preferably 23 to 27 bases, of ZFAT mRNA and an anti-sense RNA having a base sequence complementary to the base sequence of the sense RNA or a shRNA comprising a double-stranded RNA (dsRNA) with the sense RNA connected to the anti-sense RNA via a loop sequence.
The inhibitory RNA for inhibiting the expression of ZFAT gene according to this invention decreases a rate of cell proliferation of cancer cells, etc., induces apoptosis of cells including cancer cells, or inhibits an immunoresponse by inhibiting the expression of the ZFAT gene. Therefore, the inhibitory RNA of this invention is useful for development of molecular target agents particularly for cancer cells or immunosuppressive agents.

21 Claims, 10 Drawing Sheets

Fig. 4
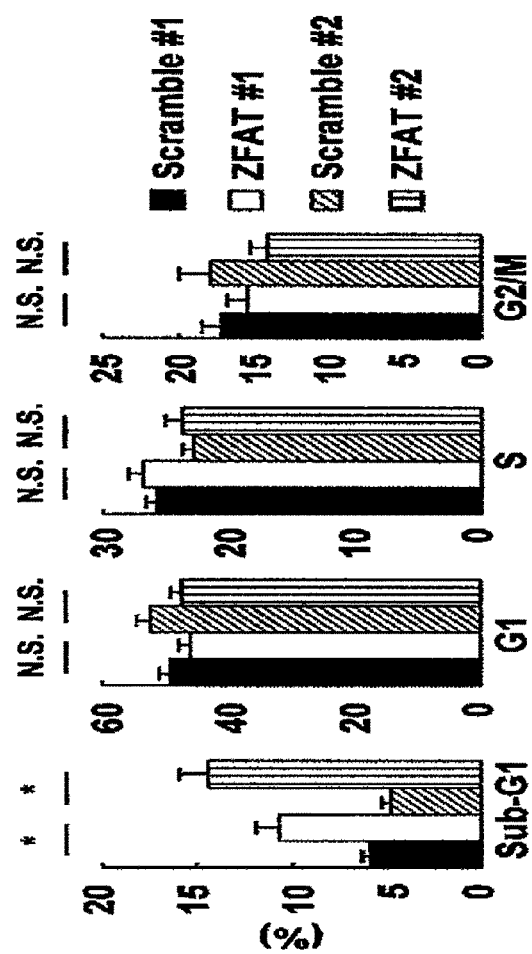
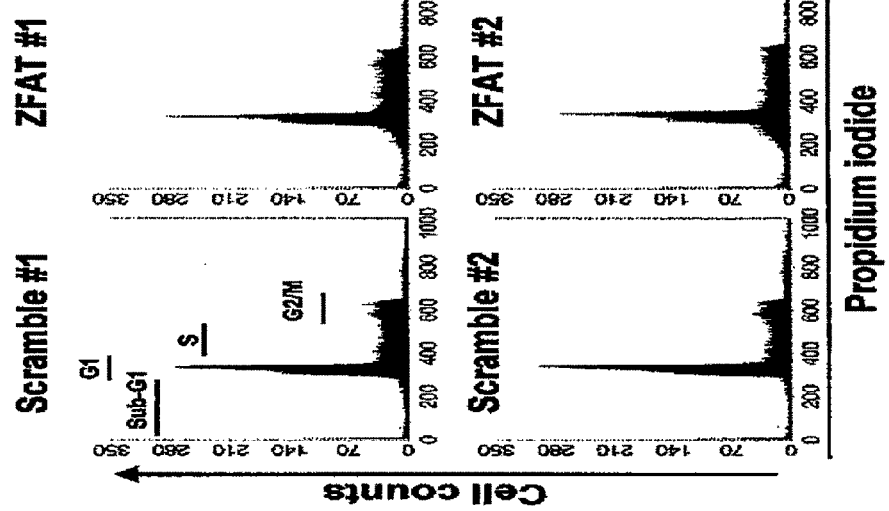

DETECTION OF APOPTOSIS CELLS BY ANNEXIN V STAINING

Fig. 7
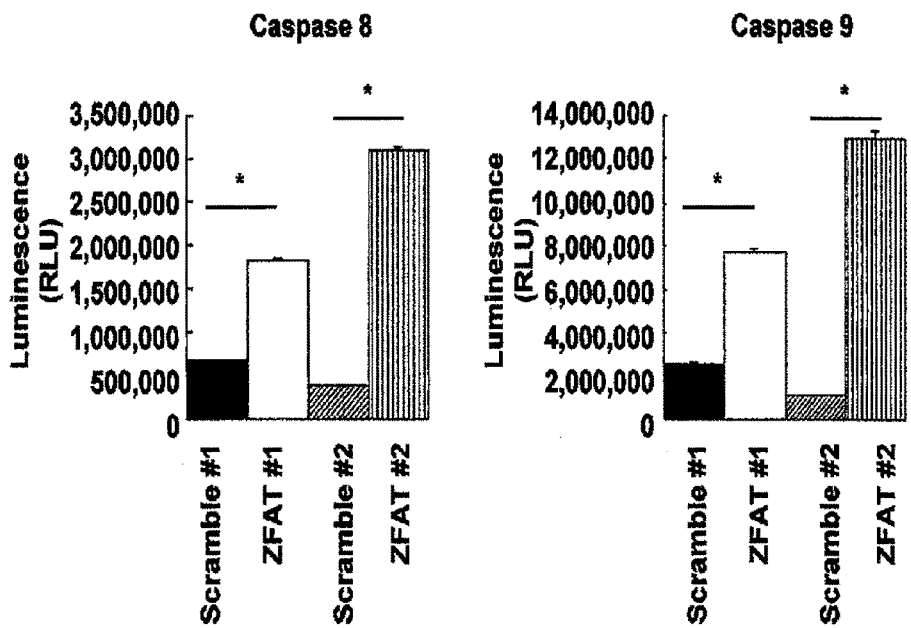
Fig. 8
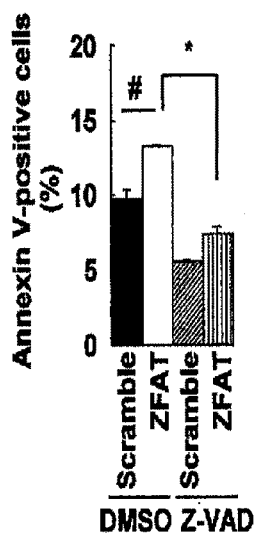
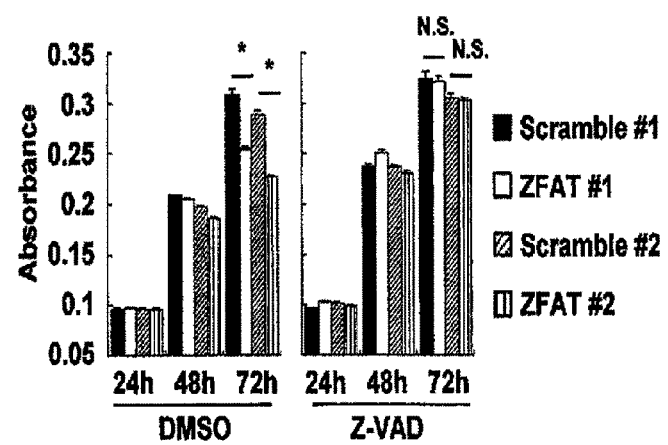

Fig. 9
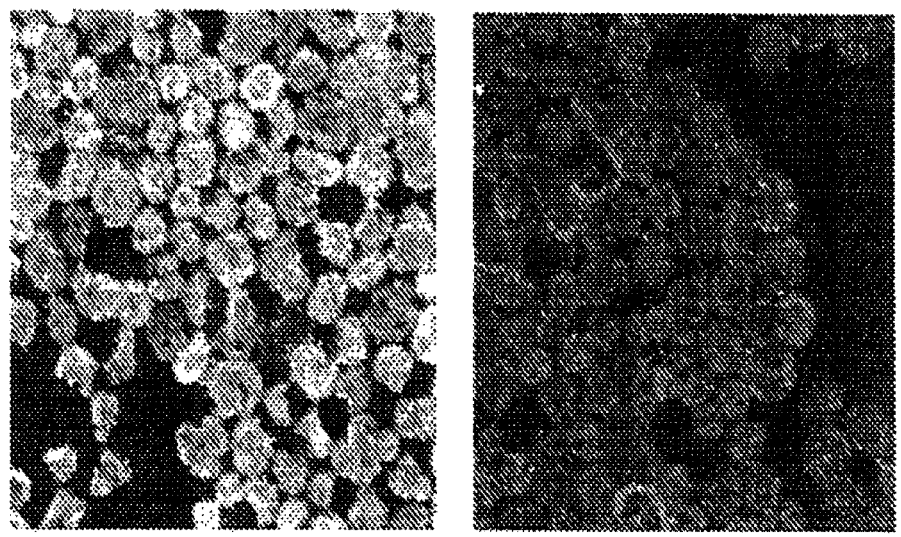
Control siRNA      hZFAT siRNA#5
MOLT4 ZFAT-siRNA (48h)
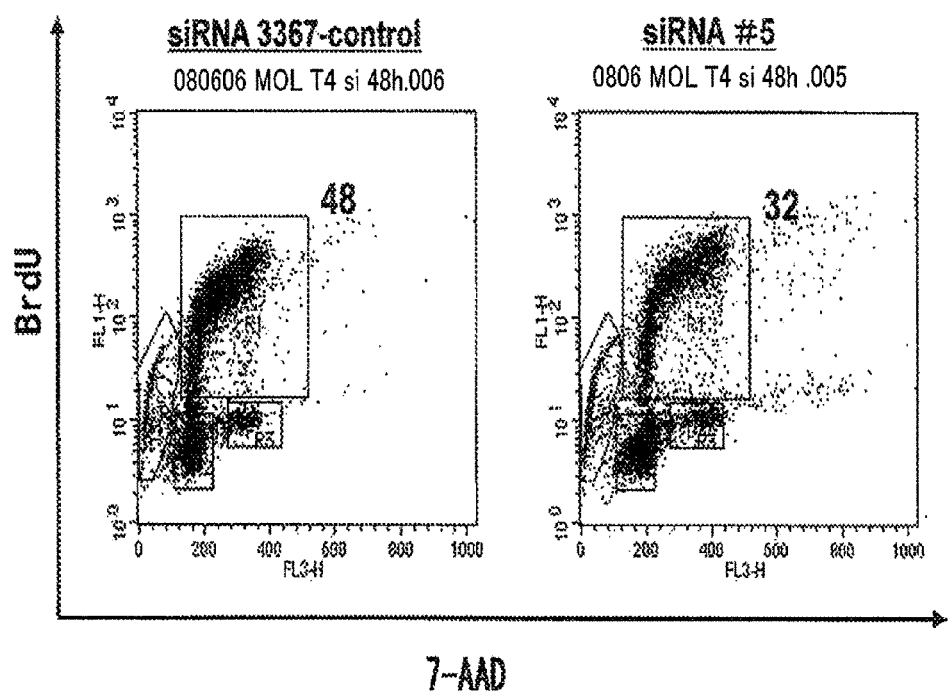

SEQUENCE LISTING

```
<160> NUMBER OF SEQ ID NOS: 30

<210> SEQ ID NO 1
<211> LENGTH: 25
<212> TYPE: RNA
<213> ORGANISM: Artificial Sequence
<220> FEATURE:
<223> OTHER INFORMATION: 200 ZFAT sense

<400> SEQUENCE: 1
acggccaucu uuauguguaa auguu                                          25

<210> SEQ ID NO 2
<211> LENGTH: 25
<212> TYPE: RNA
<213> ORGANISM: Artificial Sequence
<220> FEATURE:
<223> OTHER INFORMATION: 200 ZFAT antisense

<400> SEQUENCE: 2
aacauuuaca cauaaagaug gccgu                                          25

<210> SEQ ID NO 3
<211> LENGTH: 25
<212> TYPE: RNA
<213> ORGANISM: Artificial Sequence
<220> FEATURE:
<223> OTHER INFORMATION: 319 ZFAT sense

<400> SEQUENCE: 3
ccuuaggccu cugaguacac cugaa                                          25
```

```
<210> SEQ ID NO 4
<211> LENGTH: 25
<212> TYPE: RNA
<213> ORGANISM: Artificial Sequence
<220> FEATURE:
<223> OTHER INFORMATION: 319 ZFAT antisense

<400> SEQUENCE: 4
uucaggugua cucagaggcc uaagg                                          25

<210> SEQ ID NO 5
<211> LENGTH: 25
<212> TYPE: RNA
<213> ORGANISM: Artificial Sequence
<220> FEATURE:
<223> OTHER INFORMATION: 519 ZFAT antisense

<400> SEQUENCE: 5
gggaagcagu uuaagugcac ggugu                                          25

<210> SEQ ID NO 6
<211> LENGTH: 25
<212> TYPE: RNA
<213> ORGANISM: Artificial Sequence
<220> FEATURE:
<223> OTHER INFORMATION: 3062 ZFAT sense

<400> SEQUENCE: 6
acaccgugca cuuaaacugc uuccc                                          25

<210> SEQ ID NO 7
<211> LENGTH: 25
<212> TYPE: RNA
<213> ORGANISM: Artificial Sequence
<220> FEATURE:
<223> OTHER INFORMATION: 3367 ZFAT sense

<400> SEQUENCE: 7
uggcuugaag gugguggaaa uugau                                          25

<210> SEQ ID NO 8
<211> LENGTH: 25
<212> TYPE: RNA
<213> ORGANISM: Artificial Sequence
<220> FEATURE:
<223> OTHER INFORMATION: 3367 ZFAT antisense

<400> SEQUENCE: 8
aucaauuucc accaccuuca agcca                                          25

<210> SEQ ID NO 9
<211> LENGTH: 25
<212> TYPE: RNA
<213> ORGANISM: Artificial Sequence
<220> FEATURE:
<223> OTHER INFORMATION: 200 ZFAT control sense

<400> SEQUENCE: 9
acgaccuuua uguguauaau cgguu                                          25

<210> SEQ ID NO 10
<211> LENGTH: 25
<212> TYPE: RNA
<213> ORGANISM: Artificial Sequence
<220> FEATURE:
<223> OTHER INFORMATION: 200 ZFAT control antisense
```

-continued

```
<400> SEQUENCE: 10
aaccgauuau acacauaaag gucgu                                              25

<210> SEQ ID NO 11
<211> LENGTH: 25
<212> TYPE: RNA
<213> ORGANISM: Artificial Sequence
<220> FEATURE:
<223> OTHER INFORMATION: 319 ZFAT control sense

<400> SEQUENCE: 11
ccuccgdguc uaugaccacu augaa                                              25

<210> SEQ ID NO 12
<211> LENGTH: 25
<212> TYPE: RNA
<213> ORGANISM: Artificial Sequence
<220> FEATURE:
<223> OTHER INFORMATION: 319 ZFAT control antisense

<400> SEQUENCE: 12
uucauagugg ucauagaccc ggagg                                              25

<210> SEQ ID NO 13
<211> LENGTH: 25
<212> TYPE: RNA
<213> ORGANISM: Artificial Sequence
<220> FEATURE:
<223> OTHER INFORMATION: 3062 ZFAT control sense

<400> SEQUENCE: 13
gggacguuga augugcacgg aaugu                                              25

<210> SEQ ID NO 14
<211> LENGTH: 25
<212> TYPE: RNA
<213> ORGANISM: Artificial Sequence
<220> FEATURE:
<223> OTHER INFORMATION: 3062 ZFAT control antisense

<400> SEQUENCE: 14
acaucccgug cacauucaac guccc                                              25

<210> SEQ ID NO 15
<211> LENGTH: 25
<212> TYPE: RNA
<213> ORGANISM: Artificial Sequence
<220> FEATURE:
<223> OTHER INFORMATION: 3367 ZFAT control sense

<400> SEQUENCE: 15
aucgaauauu cccaacccuu accca                                              25

<210> SEQ ID NO 16
<211> LENGTH: 25
<212> TYPE: RNA
<213> ORGANISM: Artificial Sequence
<220> FEATURE:
<223> OTHER INFORMATION: 3367 control antisense

<400> SEQUENCE: 16
uggguaaggg uugggaauau ucgau                                              25

<210> SEQ ID NO 17
<211> LENGTH: 25
<212> TYPE: RNA
```

```
<213> ORGANISM: Artificial Sequence
<220> FEATURE:
<223> OTHER INFORMATION: 231 mFAT sense

<400> SEQUENCE: 17
cagucagaac ucgugaccca cguuu                                       25

<210> SEQ ID NO 18
<211> LENGTH: 25
<212> TYPE: RNA
<213> ORGANISM: Artificial Sequence
<220> FEATURE:
<223> OTHER INFORMATION: 231 mFZAT antisense

<400> SEQUENCE: 18
aaacgugggu cacgaguucu gacug                                       25

<210> SEQ ID NO 19
<211> LENGTH: 25
<212> TYPE: RNA
<213> ORGANISM: Artificial Sequence
<220> FEATURE:
<223> OTHER INFORMATION: 740 mZFAT sense

<400> SEQUENCE: 19
cagcgugguc uuaacugcuc augaa                                       25

<210> SEQ ID NO 20
<211> LENGTH: 25
<212> TYPE: RNA
<213> ORGANISM: Artificial Sequence
<220> FEATURE:
<223> OTHER INFORMATION: 740 mZFAT antisense

<400> SEQUENCE: 20
uucaugagca guuaagacca cgcug                                       25

<210> SEQ ID NO 21
<211> LENGTH: 25
<212> TYPE: RNA
<213> ORGANISM: Artificial Sequence
<220> FEATURE:
<223> OTHER INFORMATION: 3469 mZFAT sense

<400> SEQUENCE: 21
ccgcugugaa uauccugcag cagau                                       25

<210> SEQ ID NO 22
<211> LENGTH: 25
<212> TYPE: RNA
<213> ORGANISM: Artificial Sequence
<220> FEATURE:
<223> OTHER INFORMATION: 3469 mZFAT antisense

<400> SEQUENCE: 22
aucugcugca ggauauucac agcgg                                       25

<210> SEQ ID NO 23
<211> LENGTH: 25
<212> TYPE: RNA
<213> ORGANISM: Artificial Sequence
<220> FEATURE:
<223> OTHER INFORMATION: 231 mZFAT control sense

<400> SEQUENCE: 23
cagagaacuc gugacccacg ucuuu                                       25
```

```
<210> SEQ ID NO 24
<211> LENGTH: 25
<212> TYPE: RNA
<213> ORGANISM: Artificial Sequence
<220> FEATURE:
<223> OTHER INFORMATION: 231 mZFAT control antisense

<400> SEQUENCE: 24
aaagacgugg gucacgaguu cucug                                          25

<210> SEQ ID NO 25
<211> LENGTH: 25
<212> TYPE: RNA
<213> ORGANISM: Artificial Sequence
<220> FEATURE:
<223> OTHER INFORMATION: 740 mZFAT control sense

<400> SEQUENCE: 25
cagugguauu cgucaacucu gcgaa                                          25

<210> SEQ ID NO 26
<211> LENGTH: 25
<212> TYPE: RNA
<213> ORGANISM: Artificial Sequence
<220> FEATURE:
<223> OTHER INFORMATION: 740 mZFAT control antisense

<400> SEQUENCE: 26
uucgcagagu ugacgaauac cacug                                          25

<210> SEQ ID NO 27
<211> LENGTH: 50
<212> TYPE: DNA
<213> ORGANISM: Artificial Sequence
<220> FEATURE:
<223> OTHER INFORMATION: 556 mZFAT top

<400> SEQUENCE: 27
caccgcaagc acatctgcat cattgcgaac aatgatgcag atgtgcttgc               50

<210> SEQ ID NO 28
<211> LENGTH: 50
<212> TYPE: DNA
<213> ORGANISM: Artificial Sequence
<220> FEATURE:
<223> OTHER INFORMATION: 556 mZFAT bottom

<400> SEQUENCE: 28
aaaagcaagc acatctgcat cattgttcgc aatgatgcag atgtgcttgc               50

<210> SEQ ID NO 29
<211> LENGTH: 50
<212> TYPE: DNA
<213> ORGANISM: Artificial Sequence
<220> FEATURE:
<223> OTHER INFORMATION: mZFAT control top

<400> SEQUENCE: 29
caccaagaca atcggctgct ctgatcgaaa tcagagcagc cgattgtctt               50

<210> SEQ ID NO 30
<211> LENGTH: 50
<212> TYPE: DNA
<213> ORGANISM: Artificial Sequence
<220> FEATURE:
<223> OTHER INFORMATION: mZFAT Control bottom
```

```
<400> SEQUENCE: 30
aaaaaagaca atcggctgct ctgatttcga tcagagcagc cgattgtctt            50
```

INHIBITORY RNA FOR MODULATING THE MOLECULAR FUNCTION OF ZFAT GENE

TECHNICAL FIELD

This invention relates to an inhibitory RNA for modulating the molecular function of ZFAT gene and, more particularly, to an inhibitory RNA for inhibiting the expression of ZFAT gene capable of inhibiting cell proliferation or inducing apoptosis, an expression vector containing the same, a method for inhibiting the expression of ZFAT gene using the same, a cell proliferation inhibiting method, and an apoptosis induction method by inhibiting the expression of ZFAT gene, as well as a medical composition containing the inhibitory RNA for inhibiting the expression of ZFAT gene.

BACKGROUND TECHNOLOGY

The understanding of molecular identification and molecular mechanisms regarding proliferation, apoptosis, differentiation, etc., leads to the understanding of malignant transformation and pathological conditions of cells. Modifications of molecular function (molecular target) focusing on particular genes or signal channels are one of methods for artificially controlling dynamics of cells and normalizing pathological conditions of cells.

Many anti-cancer agents as have been applied so far are derived from natural substances and chemical compounds. They, however, have drawbacks that they may react to cancer cells and to normal cells, too, causing severe side effects. Recent years, therefore, trials have been made of clinical applications of molecular target agents with the attempt to reduce such side effects, however, the current state of such molecular target agents is not yet satisfactory in terms of efficacy and reduction of side effects.

ZFAT gene (zinc-finger gene in autoimmune thyroid disease susceptibility region: ZNF406) identified as a gene associated with autoimmune thyroid diseases is a Zn finger protein coding for a protein composed of 1,243 amino acid residues and having one AT hook domain and 18 Zn finger domains. The distribution of the ZFAT proteins in mouse tissues is characterized in that it is strongly expressed in the thymus gland and the spleen yet the expressing cells are limited to B cells and T cells (Non-Patent Literature No. 1). The mechanism of ZFAT protein is not yet identified.

RNAi (RNA interference) is noted as an effective method for analyzing genetic functions. RNAi is a phenomenon in that a double-stranded RNA (dsRNA) consisting of a sense RNA and an anti-sense RNA, homologous to a gene, destroys a homologous portion of a transcription product (mRNA) of the gene, thus leading to inhibition of the expression of a gene having a sequence identical thereto, that is, to inhibition of the synthesis of a protein (for example, Non-patent Literature Nos. 2, 3, 4). In other words, RNAi is a unique method that can search for functions of genes by performing a knock-out of (destroying) mRNA of a target gene having a known sequence.

Further, RNAi can confirm results at a cell level so that it is advantageous to achieve result in more precise way, at lower costs and in shorter time, compared to conventional gene knock-out method that confirms results using animals. In addition thereto, the RNAi method has the merits that results can be expected to be achieved at a low concentration, and only mRNA can be destroyed without affecting any adverse influence on the genomic gene itself.

[Non-patent Literature No. 1] Koyanagi, M., Nakabayashi, K., Fujimoto, T., Gu, N., Baba, I., Takashima, Y., Doi, K., Harada, H., Kato, N., Sasazuki, T., and Shirasawa, S. (2008) Genomics 91, 451-457

[Non-patent Literature No. 2] Fire, A/, et al: Nature (1998) 391:806-811

[Non-patent Literature No. 3] Ui-Tei, K., et al: FEBS Lett (2000) 479: 79-82

[Non-patent Literature No. 4] Elbashir S M., et al: Nature (2001) 411:494-498

DISCLOSURE OF INVENTION

As a result of extensive review and study of ZFAT gene, the present inventors have conducted a further analysis utilizing RNAi techniques assuming that a ZFAT protein plays a significant function in immune reaction on the basis that it is expressed strongly in human leukemia cells and at the time of immunoresponse (at the time of stimulation of blast formation) found that siRNA (small interfering RNA), i.e., a double-stranded RNA composed of a sense RNA homologous to the ZFAT gene and an anti-sense RNA, inhibits the expression of ZFAT gene. It has further been found that inhibition of the expression of the ZFAT gene induces apoptosis of cancer cells and inhibits immunoresponse in naïve CD4 positive T cells. As a result, the present inventors have found that the inhibitory RNA for inhibiting the expression of ZFAT gene may be used as a molecular target agent or an immunosuppressive agent having a higher selectivity by controlling an amount and function of the ZFAT gene. This invention has been completed based on these findings.

Therefore, this invention has an object to provide an inhibitory RNA for inhibiting the expression of ZFAT gene comprising a double-stranded RNA composed of a sense RNA homologous to ZFAT gene and an anti-sense RNA thereto.

This invention, as its preferred embodiment, has another object to provide the inhibitory RNA for inhibiting the expression of ZFAT gene including a double-stranded RNA consisting of a sense RNA with a base sequence of contiguous 20 to 30 bases, preferably 23 to 27 bases, of ZFAT gene and the anti-sense RNA with a base sequence complementary to the base sequence of the sense RNA, and a shRNA (short hairpin RNA) having a hairpin structure formed by connecting the sense RNA to the anti-sense RNA through a spacer oligonucleotide.

This invention, as its another aspect, has a further object to provide an expression vector capable of expressing the inhibitory RNA for inhibiting the expression of ZFAT gene.

This invention, as its another aspect, has a further object to provide a method for inhibiting the expression of ZFAT gene in cells by introducing the inhibitory RNA for inhibiting the expression of ZFAT gene or the expression vector into cells.

This invention, as its another aspect, has a further object to provide a cell proliferation inhibiting method for inhibiting the cell proliferation of cells such as cancer cells and an apoptosis induction method for inducing apoptosis of cells such as cancer cells by introducing the inhibitory RNA for inhibiting the expression of ZFAT gene or the expression vector into cells.

This invention, as its another aspect, has a further object to provide an immunoresponse inhibiting method for inhibiting an immunoresponse in living bodies by inhibiting the immunoresponse in cells by inhibition of the expression of the ZFAT gene.

Furthermore, this invention has an object to provide a medical composition that contains the inhibitory RNA for inhibiting the expression of ZFAT gene or the expression vector and is effective for treatment or prevention of diseases including cancers by inhibiting the immunoresponse in cells by the inhibition of cell proliferation or apoptosis induction.

In order to achieve the objects as described above, this invention provides the inhibitory RNA for inhibiting the expression of ZFAT gene comprising a double-stranded RNA containing a sense RNA having a base sequence of contiguous 20 to 30 bases, preferably 23 to 27 bases, of ZFAT mRNA and an anti-sense RNA having the base sequence complementary to the base sequence of the sense RNA.

It is to be understood herein that the term "double-stranded RNA" as used herein is used to mean a siRNA composed of a sense RNA with a base sequence of contiguous 20 to 30 bases, preferably 23 to 27 bases, of ZFAT mRNA and an anti-sense RNA with a base sequence complementary to the base sequence of the sense RNA, and a shRNA with a hairpin structure formed by connecting the sense RNA to the anti-sense RNA in the form of a loop sequence through a spacer oligonucleotide as well as a dsRNA containing the siRNA or shRNA. Therefore, it is to be understood herein that the terms "inhibitory RNA for inhibiting the expression of ZFAT gene", "double-stranded RNA", "siRNA", and "shRNA", as well as their relating terms are used exchangeably herein so as to include all such meanings even if they are used singly or in combination with others, unless otherwise stated.

This invention, as its preferred embodiment, provides the inhibitory RNA for inhibiting the expression of ZFAT gene comprising a double-stranded RNA with one to six nucleotides added to each strand at its 3'-terminus.

This invention, as its further preferred embodiment, provides the inhibitory RNA for inhibiting the expression of ZFAT gene comprising a siRNA composed of the sense RNA with the base sequence of contiguous 20 to 30 bases, preferably 23 to 27 bases, of ZFAT mRNA or a shRNA consisting of the double-stranded RNA with the sense RNA and the anti-sense RNA which are connected together in the form of a loop sequence.

This invention, as its another preferred embodiment, provides the inhibitory RNA for inhibiting the expression of the ZFAT gene, comprising a human ZFAT (hZFAT) siRNA having the base sequences as indicated by SQ ID NO. 1 and 2, 3 and 4, 5 and 6, or 7 and 8, or a mouse ZFAT (mFAT) siRNA having the base sequences as indicated by SQ ID NO. 17 and 18, 19 and 20, or 21 and 22, respectively.

This invention, as its another aspect, provides an expression vector for expressing the inhibitory RNA for inhibiting the expression of ZFAT gene.

This invention, as its another aspect, provides a method for inhibiting the expression of ZFAT gene in cells by introducing the inhibitory RNA for inhibiting the expression of ZFAT gene or the expression vector into the cells.

This invention, as its further another aspect, provides a cell proliferation inhibiting method for inhibiting cell proliferation and an apoptosis induction method for inducing apoptosis of cells by introducing the inhibitory RNA for inhibiting the expression of ZFAT gene and the expression vector into the cells.

This invention, as its further another aspect, provides an immunoresponse inhibiting method for inhibiting the immunoresponse in living bodies by inhibiting the expression of ZFAT gene by introducing the inhibitory RNA for inhibiting the expression of ZFAT gene or the expression vector into cells.

This invention, as its further another aspect, provides a medical composition which contains the inhibitory RNA for inhibiting the expression of ZFAT gene or the expression vector as an active ingredient and which is effective for treatment or prevention of diseases such as cancers by inhibiting the cell proliferation of cancer cells or inducing apoptosis by inhibition of the immunoresponse in living bodies.

The inhibitory RNA for inhibiting the expression of ZFAT gene or the expression vector according to this invention have the effects on inhibition of the expression of ZFAT gene in living bodies, as well as on inhibition of the proliferation of cells such as cancer cells, or induction of apoptosis, or inhibition of an immunoresponse. Therefore, this invention can provide a medical composition having the effects on inhibition of cell proliferation, apoptosis induction, or inhibition of immunoresponse.

BRIEF DESCRIPTION OF ACCOMPANYING DRAWINGS

FIG. 4 is a view showing an influence of siRNA on a cell cycle by propidium iodide staining assay.

FIG. 7 is a view showing a mode of activation of caspase 8 and caspase 9 for apoptosis induction by inhibition of the expression of human ZFAT gene in cells.

FIG. 8 is a view showing inhibition of apoptosis induction by inhibition of the expression of ZFAT gene with a caspase inhibitor.

FIG. 9 is a view showing an influence on cell cycle at the time of inhibition of the expression of ZFAT gene in cells.

MODES FOR CARRYING OUT THE INVENTION

The inhibitory RNA for inhibiting the expression of ZFAT gene according to this invention comprises an oligonucleotide consisting of a double-stranded RNA composed of a sense RNA homologous to the ZFAT gene and an anti-sense RNA thereof. More specifically, the inhibitory RNA for inhibiting the expression of ZFAT gene according to this invention is an inhibitory RNA for inhibiting the expression of ZFAT gene comprising a double-stranded RNA composed of the sense RNA having a contiguous base sequence of ZFAT nRNA and the anti-sense RNA having the base sequence complementary to the base sequence of the sense RNA.

More specifically, the inhibitory RNA for inhibiting the expression of ZFAT gene according to this invention comprises a siRNA consisting of the double-stranded RNA containing the sense RNA with the contiguous base sequence of ZFAT mRNA and the anti-sense RNA with the base sequence complementary to the base sequence of the sense RNA, or a shRNA capable of producing the siRNA by cleavage with a biogenic enzyme in living bodies, which has a stem loop structure with the sense RNA and the anti-sense RNA connected to each other through a loop sequence and forms a structure in which the 3'-terminus of the sense RNA is connected to the 5' terminus of the anti-sense RNA through a loop sequence (a hairpin loop sequence). Furthermore, the inhibitory RNA for inhibiting the expression of ZFAT gene according to this invention may contain a double-stranded RNA (dsRNA) including the siRNA or the shRNA.

More specifically, the inhibitory RNA for inhibiting the expression of ZFAT gene according to this invention is basically an oligonucleotide comprising a double-stranded RNA with the base sequences complementary to each other, and a sense RNA structuring one strand of the double-stranded RNA contains an optional region of the base sequence of mRNA corresponding to a target structuring gene portion of the ZFAT gene. This region may be preferably selected so as to contain a region in which the GC content accounts for, e.g., approximately 30 to 60%, preferably less than approximately 50%, and have a base length with, e.g., contiguous 20 to 30 bases, preferably 23 to 27 bases, of ZFAT mRNA. The anti-sense RNA structuring the other strand of the double-stranded RNA has a base sequence complementary to the base sequence of the sense RNA. The sense RNA or the anti-sense RNA may have an additional base sequence consisting of one to six bases at its 3'-terminus.

Figure 1:
FIG. 1 is an illustrative view showing a base sequence of siRNA of human ZFAT gene.

As shown in FIG. 1, the siRNA as the inhibitory RNA for inhibiting the expression of ZFAT gene according to this invention may be preferably selected from, for example, a human ZFAT gene (NM_020863), e.g., a double-stranded RNA (ZFAT #1) consisting of a sense RNA (SQ ID NO. 1) and an anti-sense RNA (SQ ID NO. 2) each having a base length of 25 bases homologous to a contiguous 25-base sequence from the base 200 thereof; a double-stranded RNA (ZFAT #2) consisting of a sense RNA (SQ ID NO. 3) and an anti-sense RNA (SQ ID NO. 4) each having a base length of 25 bases homologous to a contiguous 25-base sequence from the base 319 thereof, a double-stranded RNA (ZFAT #4) consisting of a sense RNA (SQ ID NO. 5) and an anti-sense RNA (SQ ID NO. 6) each having a base length of 25 bases homologous to a contiguous 25-base sequence from the base 3062 thereof; or a double-stranded RNA (ZFAT #5) consisting of a sense RNA (SQ ID NO. 7) and an anti-sense RNA (SQ ID NO. 8) each having a base length of 25 bases homologous to a contiguous 25-base sequence from the base 3367 thereof. It is to be noted herein, however, that the siRNA is not limited to the foreseeing particular sequences and it may contain any one that can demonstrate functions and effects as siRNA. Such is also included within the scope of this invention.

The base sequences of the siRNAs as indicated by SQ ID NO. 1 to 8 are respectively indicated as follows:

```
SQ ID NO. 1:
5'-A CGG CCA UCU UUA UGU GUA AAU GUU-3'

SQ ID NO. 2:
5'-A ACA UUU ACA CAU AAA GAU GGC CGU-3'

SQ ID NO. 3:
5'-C CUU AGG CCU CUG AGU ACA CCU GAA-3'

SQ ID NO. 4:
5'-U UCA GGU GUA CUC AGA GGC CUA AGG-3'

SQ ID NO. 5:
5'-G GGA AGC AGU UUA AGU GCA CGG UGU-3'

SQ ID NO. 6:
5'-A CAC CGU GCA CUU AAA CUG CUU CCC-3'

SQ ID NO. 7:
5'-U GGC UUG AAG GUG GUG GAA AUU GAU-3'

SQ ID NO. 8:
5'-A UCA AUU UCC ACC ACC UUC AAG CCA-3'
```

As controls, there are prepared scramble base sequences having base sequences different from the above siRNAs corresponding thereto, respectively. Control base sequences corresponding to LFAT #1 as indicated by SQ ID NO. 1 and 2 are referred to herein as scramble #1 and indicated by SQ ID NO. 9 and 10, respectively; control base sequences corresponding to ZFAT #2 as indicated by SQ ID NO. 3 and 4 are referred to herein as scramble #2 and indicated by SQ ID NO. 11 and 12, respectively; control base sequences corresponding to ZFAT #4 as indicated by SQ ID NO. 5 and 6 are referred to herein as scramble #4 and indicated by SQ ID NO. 13 and 14, respectively; as well as control base sequences corresponding to ZFAT #5 as indicated by SQ ID NO. 7 and 8 are referred to herein as scramble #1 and indicated by SQ ID NO. 15 and 16, respectively.

```
SQ ID NO. 9:
5'-A CGA CCU UUA UGU GUA UAA UCG GUU-3'

SQ ID NO. 10:
5'-A ACC GAU UAU ACA CAU AAA GGU CGU-3

SQ ID NO. 11:
5'-C CUC CGG GUC UAU GAC CAC UAU GAA-3'

SQ ID NO. 12:
5'-U UCA UAG UGG UCA UAG ACC CGG AGG-3'

SQ ID NO. 13:
5'-G GGA CGU UGA AUG UGC ACG GAA UGU-3'

SQ ID NO. 14:
5'-A CAU CCC GUG CAC AUU CAA CGU CCC-3'

SQ ID NO. 15:
5'-A UCG AAU AUU CCC AAC CCU UAC CCA-3'

SQ ID NO. 16:
5'-U GGG UAA GGG UUG GGA AUA UUC GAU-3'
```

Figure 10:
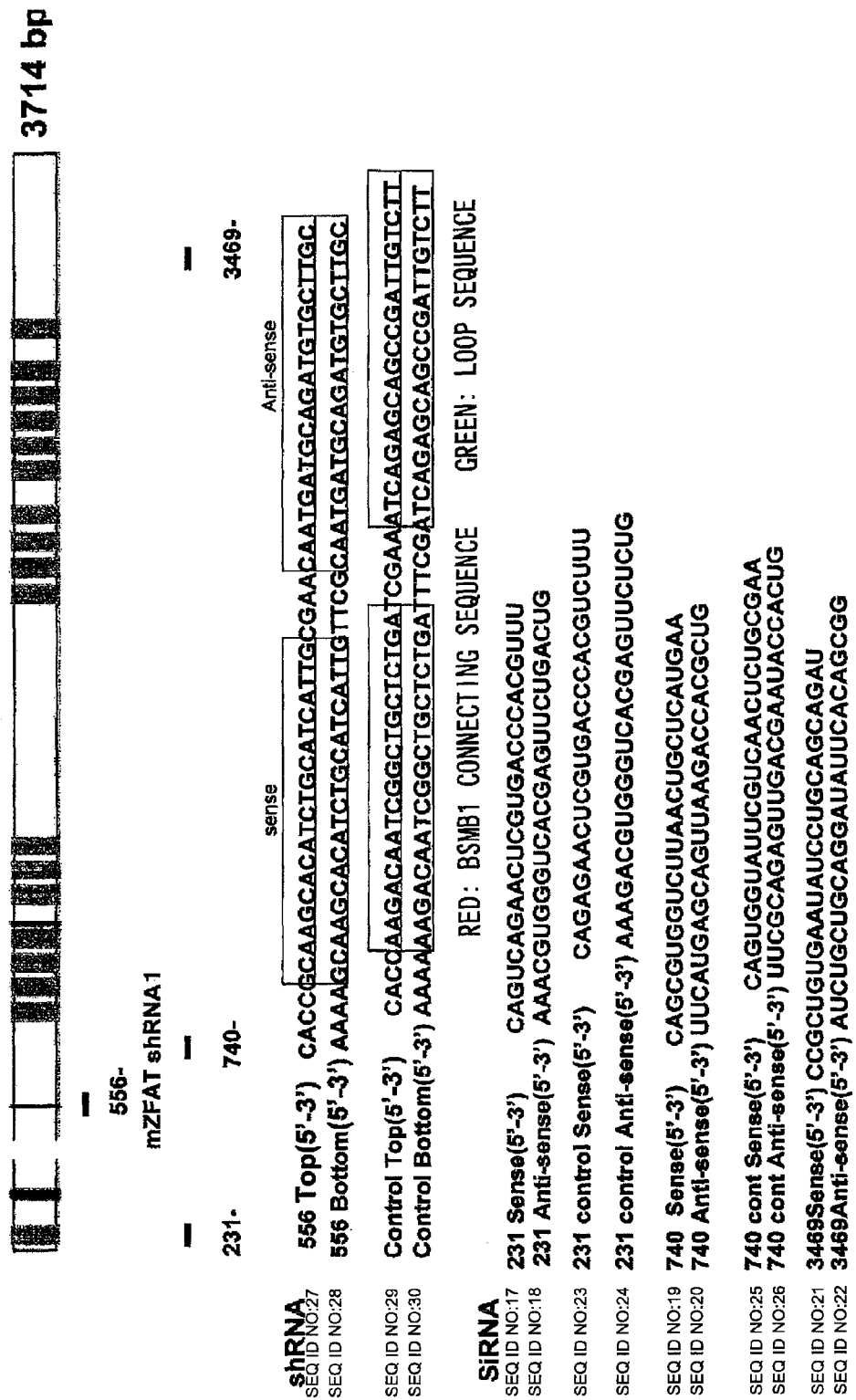
FIG. 10 is an illustrative view showing base sequences of siRNA and shRNA of mouse ZFAT gene.

It is also to be noted herein that this invention includes siRNAs from mouse ZFAT gene (NM_198644). As shown in FIG. 10, the siRNAs may include, for example, a siRNA (mZFAT 231siRNA) consisting of sense RNA (231 Sense (5'-3'); SQ ID NO. 17) with a base sequence homologous to the base sequence from base 231 of mouse ZFAT gene and anti-sense RNA (231 Anti-sense (5'-3'): SQ ID NO. 18); a siRNA (mZFAT 740siRNA) consisting of sense RNA (740 Sense (5'-3'): SQ ID NO. 19) with a base sequence homologous to the base sequence from base 740 of mouse ZFAT gene and anti-sense RNA (740 Anti-sense (5'-3'): SQ ID NO. 20); or a siRNA (mZFAT 3469siRNA) consisting of sense RNA (3469 Sense (5'-3'): SQ ID NO. 21) with a base sequence homologous to the base sequence from base 3469 of mouse ZFAT gene and anti-sense RNA (3469 Anti-sense (5'-3'): SQ ID NO. 22), resspectively.

The base sequences of the siRNAs of mouse ZFAT gene as indicated by SQ ID NO. 17 to 22 are respectively indicated as follows:

SQ ID NO. 17:
5'-CAGUCAGAACUCGUGACCCACGUUU-3'

SQ ID NO. 18:
5'-AAACGUGGGUCACGAGUUCUGACUG-3'

SQ ID NO. 19:
5'-CAGCGUGGUCUUAACUGCUCAUGAA-3'

SQ ID NO. 20:
5'-UUCAUGAGCAGUUAAGACCACGCUG-3'

SQ ID NO. 21:
5'-CCGCUGUGAAUAUCCUGCAGCAGAU-3'

SQ ID NO. 22:
5'-AUCUGCUGCAGGAUAUUCACAGCGG-3'

As negative control base sequences corresponding to mZFAT siRNAs as indicated by SQ ID NO. 17 to 20, there have been prepared control sense RNA (SQ ID NO. 23 and 24) and anti-sense RNA (SQ ID NO. 24 and 26), respectively.

SQ ID NO. 23:
5'-CAGAGAACUCGUGACCCACGUCUUU-3'

SQ ID NO. 24:
5'-AAAGACGUGGGUCACGAGUUCUCUG-3'

SQ ID NO. 25:
5'-CAGUGGUAUUCGUCAACUCUGCGAA-3'

SQ ID NO. 26:
5'-UUCGCAGAGUUGACGAAUACCACUG-3'

As described above, the inhibitory RNA for inhibiting the expression of ZFAT gene according to this invention includes a small molecular double-stranded hairpin RNA (shRNA) producing siRNA by cleavage with an intracellular enzyme (dicer) in living bodies. The shRNA has a stem loop structure in which the sense RNA containing the double-stranded portion is connected to the anti-sense RNA through a loop sequence, i.e., the 3'-terminus of the sense RNA is connected to the 5'-terminus of the anti-sense RNA through a loop sequence (a hairpin loop sequence). It is to be noted herein, however, that the hairpin loop sequence is not limited to the above particular one and may include a base sequence composed of four to seven bases including, for example, CGAA For example, as shown in FIG. 10, the shRNAs Of this invention may include a shRNA (mZFAT shRNA #1) consisting of sense RNA (556 Top (5'-3'): SQ ID NO. 27) having a base sequence homologous to the base sequence from base 556 of mouse ZFAT gene and anti-sense RNA (556 Bottom (5'-3'): SQ ID NO. 28). As a negative control, there has mentioned a shRNA consisting of sense RNA (Control Top (5'-3'): SQ ID NO. 29) and anti-sense RNA (Control Bottom (5'-3'): SQ ID NO. 30).

As the siRNAs of the mouse ZFAT gene according to this invention, there may be mentioned, for example, siRNA (mZFAT siRNA1) consisting of sense RNA (556 Top: SQ ID NO. 27) and anti-sense RNA (556 Bottom: SQ ID NO. 28) having each a base sequence homologous to the corresponding base sequence from base 556 of the mouse ZFAT gene, as shown in FIG. 10, As a negative control, there has been prepared siRNA (mZFAT shRNA2) consisting of control sense RNA (556 Control Top: SQ ID NO. 29) and control anti-sense RNA (556 Control Bottom: SQ ID NO. 30) having each the base sequence as indicated below.

The base sequences of the above shRNA (SQ ID NO. 27 and 28) and the negative control double-stranded RNA (SQ ID NO. 29 and 30) may be respectively indicated as follows:

SQ ID NO. 27:
5'-CACC<u>GCAAGCACATCTGCATCATTGCGAA</u>CAATGATGCAGATGTG
CTTGC-3'

SQ ID NO. 28:
5'-AAAA<u>GCAAGCACATCTGCATCATTGTT</u>CG<u>CAATGATGCAGATGTG
CTTGC</u>-3'

SQ ID NO. 29:
5'-CACC<u>AAGACAATCGGCTGCTCTGAT</u>CGAA<u>ATCAGAGCAGCCGATT
GTCTT</u>-3'

SQ ID NO. 30:
5'-AAAA<u>AAGACAATCGGCTGCTCTGAT</u>TTCG<u>ATCAGAGCAGCCGATT
GTCTT</u>-3'

Among the base sequences as indicated above, the base sequence portion underlined on the left side indicates the sense RNA portion and the base sequence portion underlined on the right side indicates the anti-sense RNA portion. The base sequence between the sense RNA and the anti-sense RNA indicates a loop sequence, and the base sequence at the 5'-terminus of the sense RNA indicates a BsmB1 connecting sequence.

The inhibitory RNA for inhibiting the expression of ZFAT gene according to this invention as indicated by the above base sequences may be prepared, for example, by chemically synthesizing the sense RNA and the anti-sense RNA in a manner known to the art, annealing the sense RNA and the anti-sense RNA synthesized above, and purifying them in a manner known to the art.

The inhibitory RNA for inhibiting the expression of ZFAT gene according to this invention may be introduced into living bodies such as, for example, cells, tissues, individuals, etc., by an expression vector capable of expressing the inhibitory RNA for inhibiting the expression of ZFAT gene. The inhibitory RNA for inhibiting the expression of ZFAT gene introduced by the expression vector into living bodies is expressed in the living bodies resulting to inhibition of the expression of the ZFAT gene. For this invention, the inhibitory RNA for inhibiting the expression of ZFAT gene according to this invention may be introduced into living bodies as it is, however, it may be preferably introduced through an expression vector in terms of persistent effects.

The expression vectors according to this invention may be produced in accordance with conventional processes. Tandem-type expression vectors may be produced, for example, by amplifying a promoter portion with primers containing a sense sequence and an anti-sense sequence by PCR, cleaving the amplified fragment with a restriction enzyme, and introducing it into a downstream portion of a promoter, such as U6 promoter, of a vector. For the tandem-type expression vectors, the sense RNA and the anti-sense RNA are transcribed in cells from two U6 promoters. On the other hand, stem-loop type expression vectors may be produced, for example, by synthesizing DNAs corresponding to the sense RNA and the anti-sense RNA, respectively, synthesizing and annealing a template DNA of a double-stranded RNA consisting of oligonucleotides containing a sense-loop-antisense sequence having a structure with the sense RNA and the anti-sense RNA connected to each other through a loop sequence, and introducing the template DNA into a downstream portion of a promoter of an expression vector, e.g., a PolIII type promoter such as U6 promoter, H1 promoter, etc. The template DNA introduced into the expression vector may produce a siRNA by transcribing a short hairpin type RNA (shRNA) with an RNA polymerase and processing it with an enzyme. As the vectors, there may be used, for example, plasmid vectors, virus vectors, and so on. The plasmid vectors may include, for example, pBAsi vector, pSUPER vector, and so on. The virus vectors may include, for example, adenovirus vectors, lentivirus vectors, retrovirus vectors, and so on.

In this invention, the siRNAs may be produced by introducing the above sense and anti-sense DNAs into respectively different expression vectors, expressing them individually in cells, and annealing them in cells. When these expression vectors are used, it is preferred that the siRNAs can be produced continuously in living bodies or cells.

It is preferred that the extent to which the inhibitory RNA for inhibiting the expression of ZFAT gene according to this invention causes an inhibition (silencing) of the expression of a target gene by RNAi (RNA interference) reaches a rate at which an amount of the expression of mRNA or protein of the target gene is inhibited by 100%, compared to the case where no RNA is introduced. Even if the inhibition rate would not be 100%, however, it may be acceptable, depending upon objects or uses, etc., in some cases where the inhibition of the expression of the target gene could be judged to occur. Therefore, the inhibition rate is not limited to a particular one. Furthermore, the rate of expression of mRNAs and proteins may be measured in accordance with conventional processes. For example, mRNAs may be measured by northern hybridization, RT-PCR, etc., and proteins may be measured by western blotting, ELISA, etc.

Figure 2:
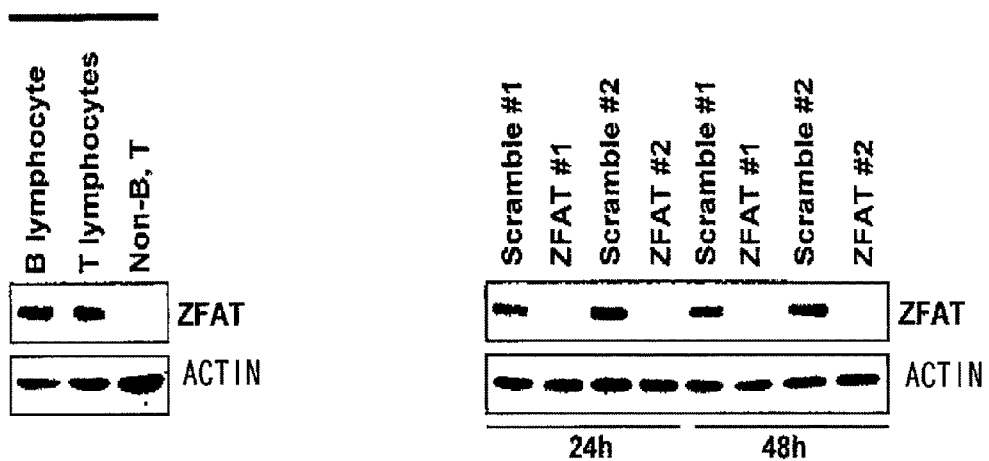
FIG. 2 is a view showing the expression of human ZFAT protein in cells (FIG. 2A) and inhibition of the expression by siRNA (FIG. 2B).
Figure 3:
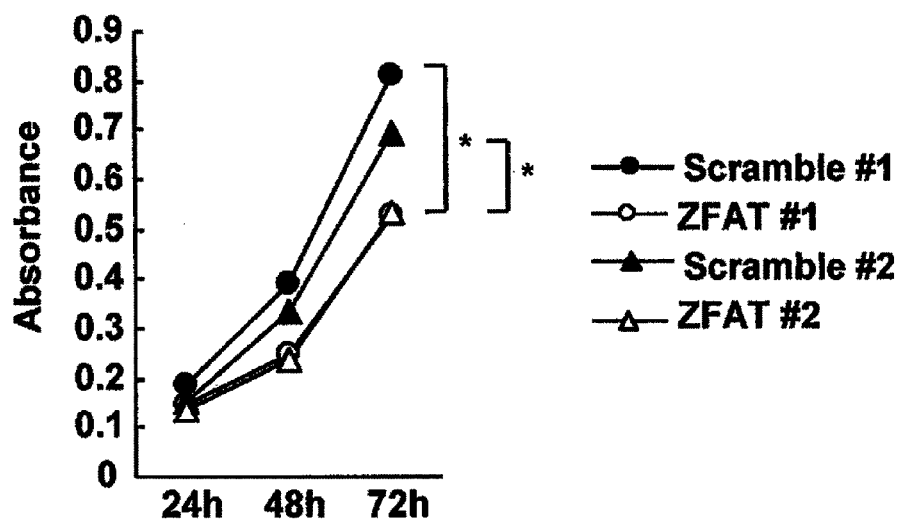
FIG. 3 is a view showing a cell proliferation ratio by inhibition of the expression of human ZFAT gene in cells.

The inhibitory RNA for inhibiting the expression of ZFAT gene according to this invention can inhibit the expression of ZFAT protein in cancer cells (FIG. 2B), and the proliferation of cancer cells can also be inhibited due to a decrease in the cell proliferation rate of cancer cells by inhibition of the expression of ZFAT gene (FIG. 3). The inhibition of the expression of ZFAT gene in cancer cells induces apoptosis (FIGS. 5 to 8) and exerts an influence on a cell cycle, leading to an increase in subG1 and earlyS fractions in flow cytometry (FIGS. 4 and 9).

In this invention, a difference in effects of target sites of ZFAT siRNA on apoptosis and cell cycle can be recognized (FIGS. 1 to 9). This indicates the possibility that the inhibitory RNA for inhibiting the expression of ZFAT gene according to this invention may be used as an inhibitor for inhibiting the amount and functions of ZFAT gene and as a molecular target agent for cancers having a high selectivity.

Figure 12:
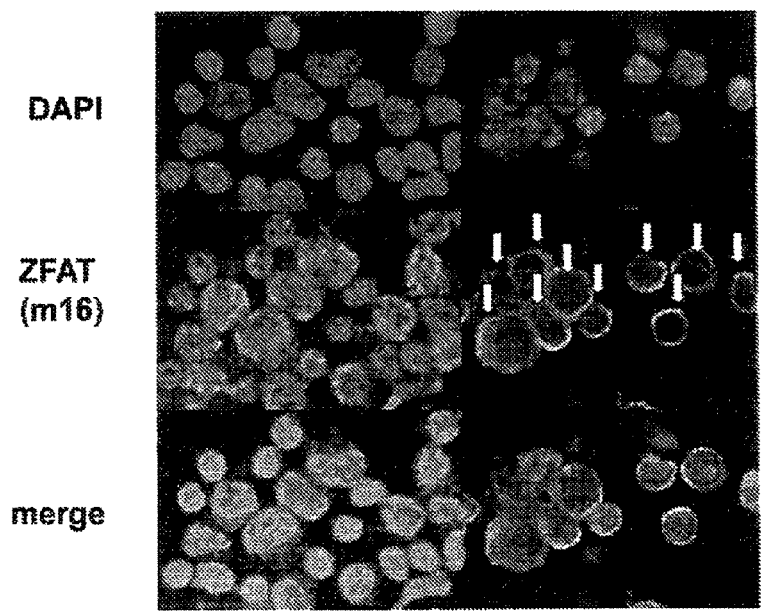
FIG. 12 is a view showing a mode of inhibition of the expression of ZFAT gene by the shRNA lentivirus as shown in FIG. 11.
Figure 13:
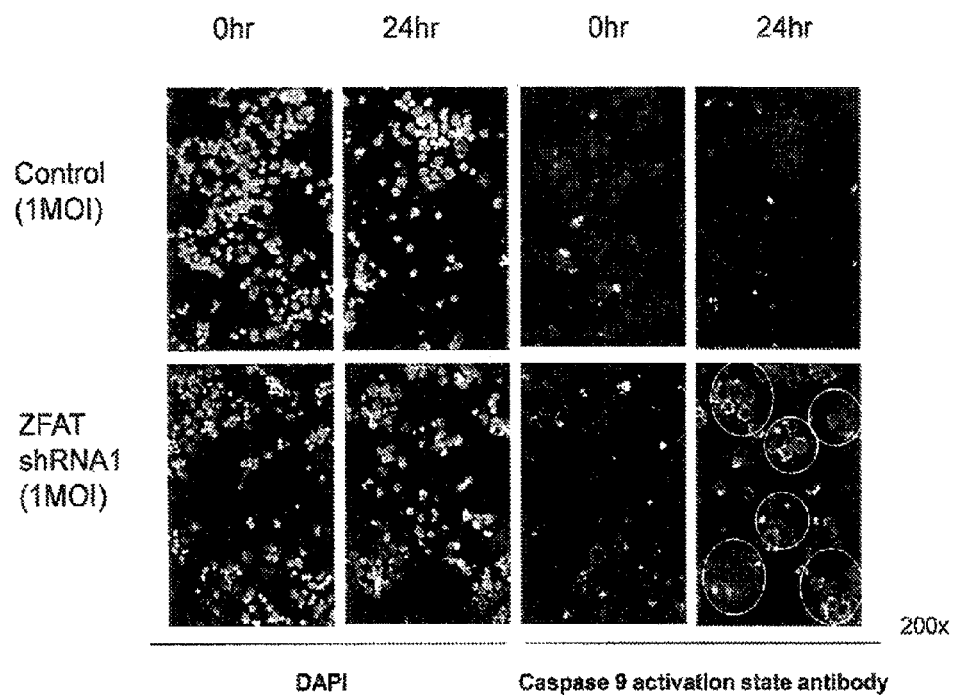
FIG. 13 is a view showing a mode of induction of activation of caspase 9 by inhibition of the expression of ZFAT gene.
Figure 14:
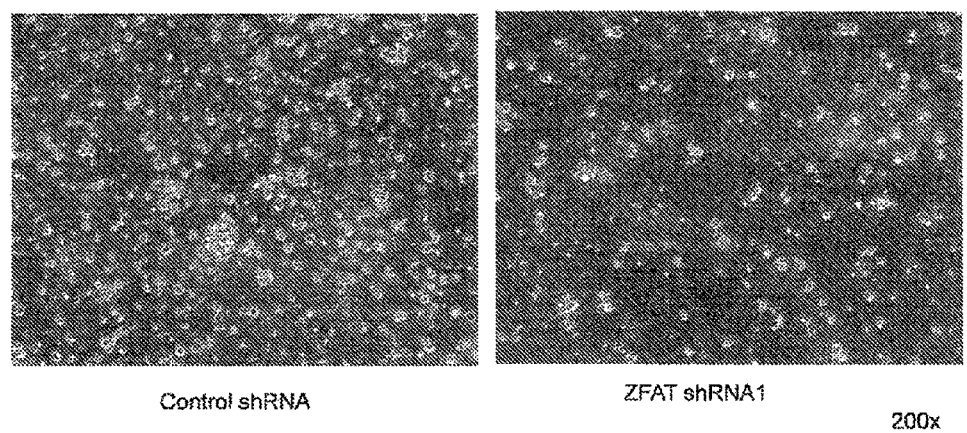
FIG. 14 is a view showing a decrease of the number of T cells after stimulation by CD3 antibody/CD28 antibody by inhibiting the expression of ZFAT gene.

Further, the inhibitory RNA for inhibiting the expression of ZFAT gene according to this invention indicates a remarkable activation of caspase 9 inducing apoptosis, compared to a control, by inhibiting the expression of ZFAT gene in naïve CD4 positive T cells of mouse peripheral blood at the time of immunoresponse (at the time of blastogenesis stimulation) by anti-CD3 antibody and anti-CD28 antibody (FIGS. 12 and 13). Thereafter, the number of living cells of the above cells decreases to a remarkable extent compared to the control (FIG. 14). This implies an increased susceptibility to apoptosis of activation-inducible T cells. This result indicates the possibility that the inhibitory RNA for inhibiting the expression of ZFAT gene according to this invention can be used as an immunosuppressive agent capable of inhibiting the rate and function of the ZFAT gene.

Therefore, this invention as another aspect provides a medical composition such as a molecular target agent or an immunosuppressive agent, which contains the inhibitory RNA for inhibiting the expression of ZFAT gene according to this invention as an active ingredient capable of inhibiting the expression of ZFAT gene. From the point of view of containing the inhibitory RNA for inhibiting the expression of ZFAT gene as an active ingredient, the expression vector for inhibiting the expression of ZFAT gene with the inhibitory RNA introduced thereinto is also encompassed within the scope of this invention.

In the event where the inhibitory RNA for inhibiting the expression of ZFAT gene or the expression vector for expressing the inhibitory RNA is applied to the medical composition such as molecular target agents or immunosuppressive agents, the inhibitory RNA or the expression vector may be administered in various routes including an oral route or a parenteral route. The preparation types for oral administration may include, for example, tablets, pills, capsules, powders, granules, syrups, and the like. The preparation types for parenteral administration may include, for example, injections, external preparations, suppositories, and the like. Whether it is administered orally or parenterally may be appropriately chosen depending upon its uses or the like. The medical composition may further contain, for example, a pharmacologically acceptable carrier including without limitation a diluent such as water, ethylalcohol, macrogol, propylene glycol, citric acid, acetic acid, phosphoric acid, lactic acid, sodium lactate, sulfuric acid, sodium hydroxide, etc., a pH adjusting agent or a buffer such as sodium citrate, sodium acetate, sodium phosphate, etc., and a stabilizer such as sodium pyrosulfite, ethylenediaminetetraacetic acid, thioglycolic acid, thiolactic acid, etc. It may also contain a sufficient amount of a compound for preparing an isotonic solution, such as salt, glucose, mannitol or glycerin. Monosacchardies such as glucose, etc., disaccharides such as saccharose, maltose, etc., sugar alcohols such as mannitol, sorbitol, etc., neutral salt such as sodium chloride, etc., amino acids such as glycine, non-ionic surfactants such as polyethylene glycol, polyoxyethylene-polyoxypropylene copolymer, polyoxyethylene sorbitan aliphatic acid ester, etc., human albumin, and so on may also be used as stabilizers. As a dose of administration may vary depending upon kinds of the active ingredients, administration routes, and ages, body weights, conditions, etc. of objects or patients, it cannot be limited to a particular one, and a daily dose may be in the range of approximately several mg to 2 grams, preferably several 10 mg, and it may be preferred to be administered once or several times per day.

The medical composition according to this invention may be prepared into formulations that can keep its stability and be delivered in a stable manner in living bodies by applying the technology of coupling with a delivery carrier such as liposome, etc., a site-specific antibody, or a cell-type specific functional peptide. Further, in order to facilitate uptake into cells, the RNA or its expression vector according to this invention may be used by preparing it in the form of a liposome.

This invention will be described more specifically by the following examples, but it is to be noted that they are solely illustrative for this invention and it is not limited in any respect to them.

Example 1

The double-stranded RNAs of human ZFAT (NM_020863) and mouse ZFAT (NM_198644) were prepared as follows. First, a sense RNA and an anti-sense RNA structuring the double-stranded RNA were chemically synthesized each in the form of oligoribonucleotide using ribonucleoside 3'-phosphoramidite and DNA/RNA synthesizer (Applide Biosystems 394 Model). After completion of the synthesis, the resulting oligoribonucleotides connected to CPG (controlled pore glass) were treated at room temperature for 2 hours in a mixed solution of concentrated ammonium water:

ethanol (3:1 v/v) and then cut off from the CPG resin, and warmed at 55° C. for another 15 hours. Thereafter, the solvent was removed off and the resulting residue was mixed with a 1M TBAF (tetrabutylammounium fluoride)/THF (tetrahydrofuran) solution and stirred at 37° C. for 16 hours. To the resulting mixture was added 0.1M triethylammonium acetate (pH 7.0), and the resulting mixture was subjected to column chromatography in a concentration gradient manner using a 5%-40% acetonitrile and 50 mM triethylammonium bicarbonate squcous solution. Fractions coloring with dimethoxytrityl were collected from the elute with an approximately 30% acetonitrile, and they were mixed with 0.01N hydrochloric acid and stirred to remove off the dimethoxytrityl group. Then, they were neutralized with 0.1N ammonium water, and the resulting aqueous layer was washed with ethyl acetate. After the solvent was removed off, they were dissolved in fertilized water. The oligoribonucleotide was separated and fractionated from the fractions by reverse HPLC and purified by subjecting it to ion-exchange HPLC, separating and fractionating it. The resulting oligoribonucleotide was used for experiments as will be described hereinunder. The sequence of the resulting oligoribonucleotide was determined by Block-it RNAi desiner (Invitrogen), and siRNA and shRNA each as indicated by the respective SQ ID NOs were annealed and purified in conventional manner.

Example 2

Figure 11:
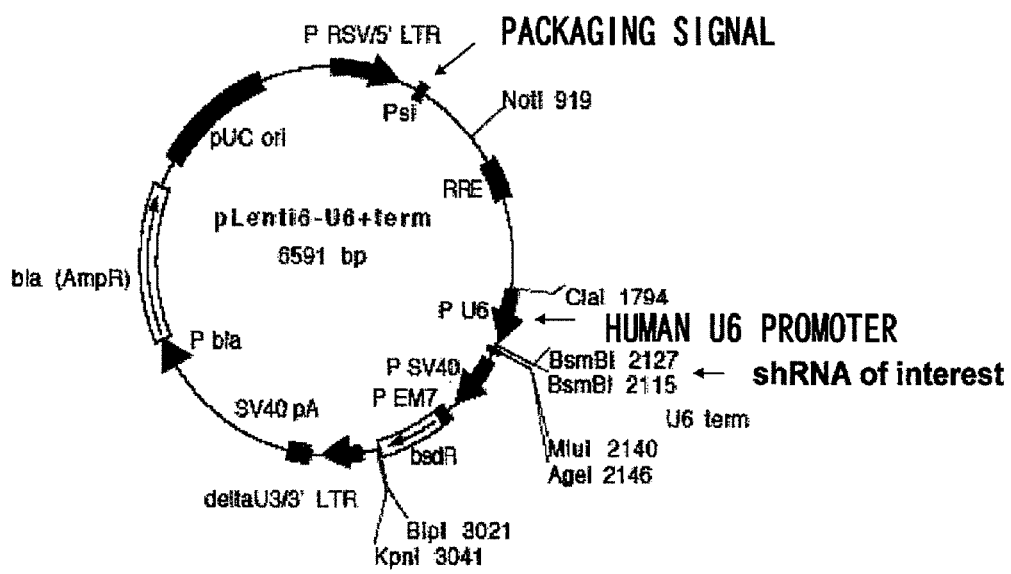
FIG. 11 is a map view showing a structure of a shRNA lentivirus with shRNA of mouse ZFAT gene introduced thereinto.

The shRNA expression vector as indicated by FIG. 11 was constructed in the manner as will be described below. Human U6 promoter (Gene bank accession #M14486 gene sequence 65-329) was inserted into ClaI and SalI sites of pLenti6/V5-Dest (Invitrogen Cat. No. 43-0315), and then U6-term was inserted into SalI and MluI sites to form pLenti6-U6+ term. The resulting pLenti6-U6+ term was then cleaved with BsmBI to form a cloning site of double-stranded synthetic oligonucleotide DNA. In order to connect he BsmBI cleavage site to the annealed oligonucleotide, sequence CACC was added to the 5'-terminus of the Top strand, and sequence AAAA was added to the 5'-terminus of the Bottom strand. The resulting sense RNA and anti-sense RNA (each having 21 bases) is formed to flank the loop sequence (5'-CGAA-3'). The base sequence was determined in accordance with a manual of Block-It U6 RNAi Entry Vector Kit (Invitrogen Cat. No. K4944-00). After the Top and Bottom strands were annealed, the resulting oligonucleotide was ligated with T4 ligase and subcloned. As a negative control, there was used eGFPshRNA consisting of Control Top sequence (SQ ID NO. 29) and Control Bottom sequence (SQ ID NO. 30).

Example 3

The proteins extracted fractions of B lymphocytes and T lymphocytes as well as other leukocytes separated from human peripheral blood were subjected to western blotting analysis.
The human peripheral blood was centrifuged with Ficoll to recover leukocytes and further treated with human CD 19 magnetic beads (Miltenyi Biotec) and human CD3 magnetic beads (Miltenyi Biotec) of MACS system (Miltenyi Biotec) to continuously separate B lymphocytes and T lymphocytes to give effluents containing neither B cell nor T cells. The resulting cells were in turn subjected to western blotting analysis, confirming that the ZFAT protein was shown to be expressed by B lymphocytes and T lymphocytes, respectively, derived from human peripheral blood (FIG. 2A).

Example 4

Two kinds of siRNA oligonucleotides (ZFAT#1 and ZFAT#2) and two kinds of control siRNA oligonucleotides (Scramble #1 and Scramble #2), each prepared by the above example, were introduced into MOLT-4 cells, and the proteins extracted therefrom at hour 24 and hour 48 after introduction were determined by subjecting them to western blotting analysis. The MOLT-4 cells were incubated at 37° C. in the presence of 5% $CO_2$ in a RPMI-1640 culture medium (GIBCO) with 10% bovine serum added thereto. The introduction of each of the siRNA oligonucleotides was performed by introducing 100 pmol of siRNA into $1 \times 10^6$ cells with MicroPorator MP-100 (Digital Bio). The proteins were extracted by using a protease inhibitor cocktel containing 50 mM Tris-HCl, pH 7.5, 150 mM NaCl, 1% NP-40, 0.5% deoxycholate, and 0.1% SDS. As an antibody, there was used anti-ZFAT rabbit polyclonal antibody produced in accordance with non-patent literature #1. As a result of western blotting analysis, it was confirmed that ZFAT expression was inhibited in MOLT-4 cells by the two siRNA oligonucleotides (ZFAT#1 and ZFAT#2) (FIG. 2B).

Example 5

Experiments were carried out as to whether the inhibition of ZFAT expression causes a decrease in the proliferation rate of MOLT-4 cells.
The siRNA oligonucleotides (ZFAT#1, ZFAT#2, Scramble#1, and Scramble#2) prepared in Example 1 were introduced each into MOLT-4 cells which were in turn inoculated into a 24-well plate at the rate of $5 \times 10^4$ cells per well, and the number of cells was counted periodically (hour 24, 48 and 72 after inoculation) with cell counting kit (DOJIN). The results are shown in FIG. 3. As a result, it was confirmed that the group of inhibition of the expression of ZFAT caused a decrease in cell proliferation, compared to the control group.

Example 6

Analysis of a cell cycle (an increase in the Sub-G1-entry) in cells inhibiting the expression of ZFAT was carried out in the manner as will be described below.
The siRNA oligonucleotides (ZFAT#1, ZFAT#2, Scramble#1, and Scramble#2) prepared in Example 1 were introduced each into MOLT-4 cells and fixed with 70% ethanol (48 hours, −20° C.) at hour 48. Then, the cells were treated at 37° C. for 1 hour with 1 □g/ml RNase and stained with propidium iodide (10 □g/ml). Thereafter, the cell cycle analysis was carried out by measuring the amount of DNA with flow cytometry. As a result, it was confirmed that the group of cells inhibiting the expression of ZFAT increased a rate of the Sub-G1 entry, compared to the control group, but it did not recognize any increase in other cell cycles (FIG. 4).

Example 7

Figure 5:
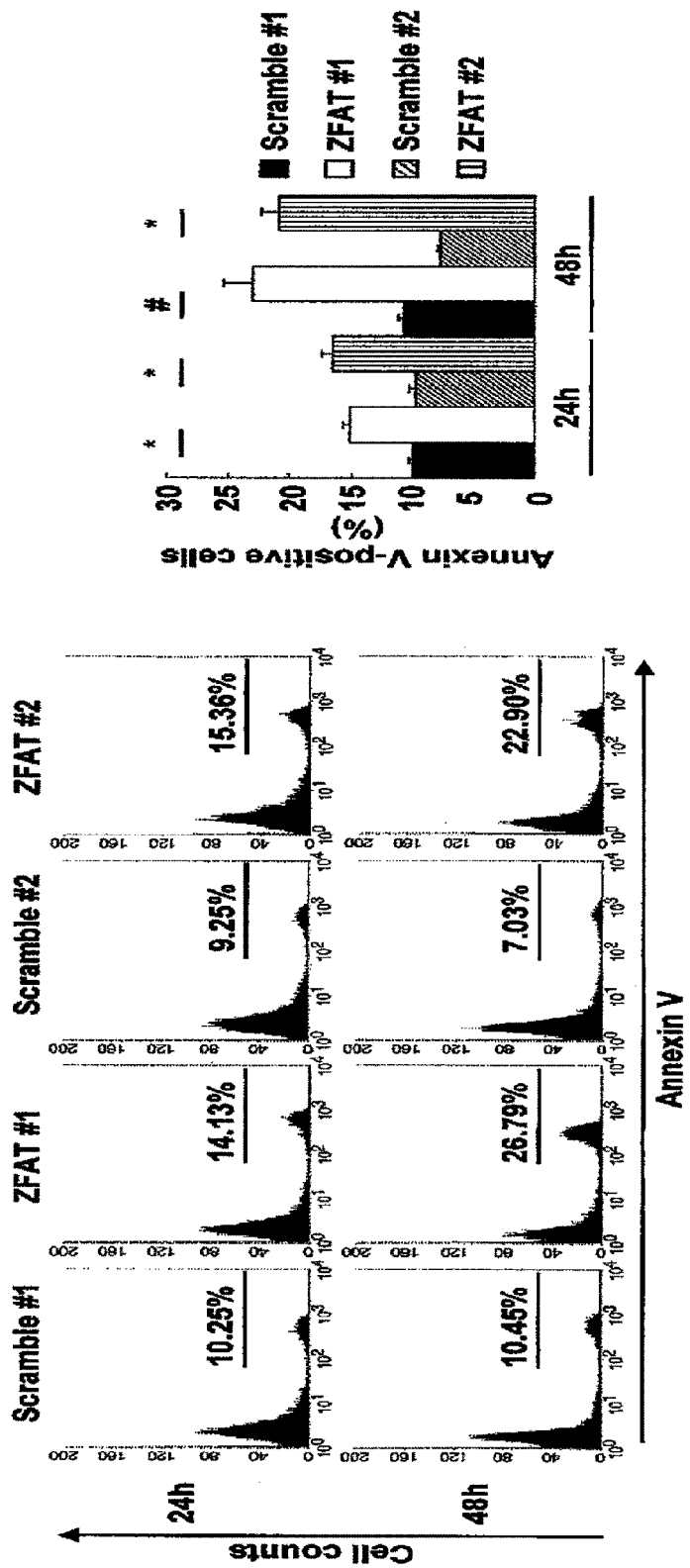
FIG. 5 is a view showing apoptosis induction by inhibition of the expression of human ZFAT gene in cells.

Experiments were carried out to confirm apoptosis induction in cells inhibiting the expression of ZFAT.
The siRNA oligonucleotides (ZFAT#1, ZFAT#2, Scramble#1, and Scramble#2) prepared in Example 1 were introduced each into MOLT-4 cells and stained with anexin V at hour 24 and hour 48 after introduction. Then, the annexin V positive cells was subjected to flow cytometry using TACS Annexin V Kit (TREVIGEN) and counted the number of the apoptosis positive cells. As a result, it was found that the group of the cells inhibiting the expression of ZFAT caused an increase apoptosis to a significant extent, compared to the control group, as shown in FIG. 5.

Example 8

This example is directed to experiments for detecting active-type caspase 3 in cells inhibiting the expression of ZFAT.

Figure 6:
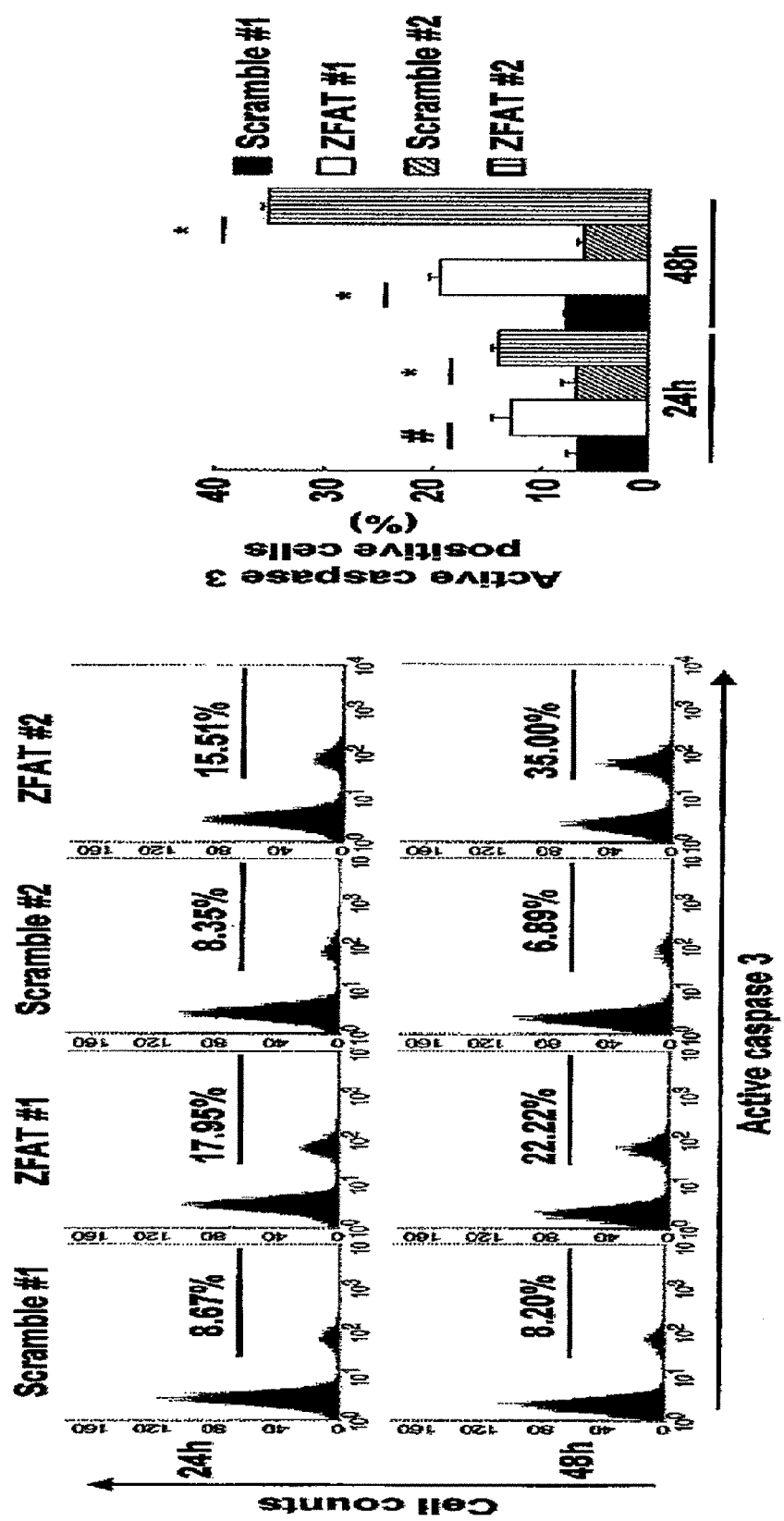
FIG. 6 is a view showing a mode of activation of caspase 3 for apoptosis induction by inhibition of the expression of human ZFAT gene in cells.

The siRNA oligonucleotides (ZFAT#1 and ZFAT#2) and the corresponding scramble sequences (Scramble#1 and Scramble#2), each prepared in Example 1, were introduced each into MOLT-4 cells, and the cells were collected at hour 24 and 48 after introduction and then stained with active-type caspase 3 antibody, detecting caspase 3 positive cells by flow cytometry using Active Caspase-3 PE MAb Apoptosis Kit (BD Pharmingen). As a result, it was found that the group of the cells inhibiting the expression of ZFAT increased the number of the caspase 3 positive cells compared to the control group (FIG. 6). As a result, it was recognized that the cells possessed a signal transduction pathway inducing apoptosis due to the fact that the active caspase 3 was detected in the cells inhibiting the expression of ZFAT. This confirms that the apoptosis in the cells inhibiting the expression of ZFAT is induced by activation of caspase 3.

Example 9

This example was carried out to determine activity of caspase 8 and caspase 9 in cells inhibiting the expression of ZFAT.

The siRNA oligonucleotides (ZFAT#1 and ZFAT#2) and the corresponding scramble sequences (Scramble#1 and Scramble#2), each prepared in Example 1, were introduced each into MOLT-4 cells, and the activity of caspase 8 (FIG. 7A) and caspase 9 (FIG. 7B) was measured by Caspase-Glo 8 Assay (Promega) and Caspase-glo 9 Assay (Promega), respectively, at hour 48 after introduction. As a result, it was recognized that the group of the cells inhibiting the expression of ZFAT increased the activity of caspase 8 and caspase 9 compared to the control group. This confirms that apoptosis was induced remarkably by inhibition of the expression of ZFAT via the activation of caspase 8 and caspase 9.

Example 10

This example was carried out to show that apoptosis to be induced by inhibition of the expression of ZFAT is inhibited by caspase inhibitor Z-VAD.

The siRNA oligonucleotides (ZFAT#2 and Scramble#2), each prepared in Example 1, were introduced each into MOLT-4 cells in the presence of the caspase inhibitor Z-VAD or DMSO as a control. The cells were then stained with annexin V to determine the apoptosis posive cells at hour 24 after introduction. As a result, it was observed that apoptosis was inhibited to a significant extent in the presence of the caspase inhibitor Z-VAD (FIG. 8A).

The siRNA oligonucleotides (ZFAT#1, ZFAT#2, Scramble#1 and Scramble#2), each prepared in Example 1, were introduced each into MOLT-4 cells in the presence of caspase inhibitor Z-VAD or DMSO, as a control, and the number of the cells was counted periodically by cell counting kit (DORN). As a result, it was observed that the inhibition of cell proliferation by inhibition of the expression of ZFAT was hindered thoroughly by the caspase inhibitor Z-VAD Z (FIG. 8B).

Example 11

This example was caned out to conduct a cell cycle analysis at the time of inhibition of the expression of ZFAT with ZFAT siRNA targeting the C-terminal region of ZFAT gene.

Human ZFAT (hZFAT) siRNA #5 (and Scramble sequence as a control) prepared in Example 1 and targeting the C-terminal region of ZFAT were introduced each into MOLT-4 cells and immunostained with anti-ZFAT antibody (M16) at hour 48 after introduction. As a result, the inhibition of the expression of ZFAT with ZFAT siRNA was confirmed (FIG. 9A). The immunostaining was carried out using ZFAT-specific antibody (M16) (1:100) and detected with anti-rat alexa 488 antibody (1:200).

ZFAT (hZFAT) siRNA #5 (and Scramble sequence as a control) targeting the C-terminal region of ZFAT were introduced each into MOLT-4 cells, and subjected to a cell cycle analysis with BrdU Flow Kit (BD Pharmingen) at hour 48 after introduction. This analysis result indicates that a transferal to the early S-entry for control was inhibited at the time of inhibition of ZFAT (FIG. 9B).

Example 12

This example was carried out to show transduction of shRNA expression vector constructed in Example 2 above. The double-stranded synthetic oligonucleotide DNA synthetized by annealing the oligonucleotide DNA prepared in Example 1 was cloned in the vector (pLenti6-U6+ term) constructed above and transfected in 293FT cells with Lyofectamin™ 2000 (Invitrogen), together with VitraPower™ packaging plasmid (Invitrogen). After 48 hours, a medium supernatant containing virus was collected, a titer was measured, and the CD4 positive cells were transducted in CD4 positive cells which were in turn separated from mouse spleen cells using mouse CD4 (L3T4) magnetic beads.

The separated CD4 positive cells were incubated in a RPMI-1640 medium (10% FCS, 50 □M 2-ME) containing IL-7 (5 ng/ml), and they were treated for 3 hours with 8 ug/ml of polybrene, followed by transduction with a virus supernatant of MOI=1, while IL-7 was administered continuously. After another 72 hours, the CD4 positive cells were inoculated on a plate coated at the rate of 1 ug/ml with anti-CD3 antibody (145-2C11; BD Pharmingen), and stimulation with RPMI-1640 containing anti-CD28 antibody (37.51; BD Pharmingen) was started.

Example 13

This example was carried out to determine inhibition of the expression of ZFAT by the shRNA expessing vector formed in Example 2. The shRNA expressing vector was transducted into CD4 positive cells and stimulated with anti-CD3 antibody and anti-CD28 antibody at hour 48 after transduction. Then, the nuclear staining was carried out for an immunostained pattern and DAPI pattern with anti-ZFAT antibody (m16) at day 2 after stimulation. The expression of ZFAT with ZFAT shRNA was inhibited for a control (eGFP shRNA) (FIG. 12). It was found as a result that the expression site of ZFAT was mainly a nucleus, and most signals of the cytoplasm were considered to be non-specific. Although the nuclear signals were observed for the control, the nuclear signals were little recognized for ZFAT shRNA.

Example 14

This example was carried out to show an influence of the shRNA expression vector constructed in Example 2 on inhibition of the expression of ZFAT at the time of stimulation of CD4 positive cells with anti-CD3 antibody and anti-CD28 antibody. At hour 72 after transduction of the shRNA expression vector into CD4 positive cells, the transducted expression vector was stimulated with anti-CD3 antibody and anti-CD28 antibody, and the DAPI pattern and immunostained pattern were investigated at hour 0.24 after stimulation (FIG. 13). For control (eGFP shRNA), activation of caspase after stimulation was not induced. On the other hand, ZFAT shRNA induces activation of caspase 9 obviously at hour 24 after stimulation. This implies that the ZFAT shRNA increases susceptivity of inhibition of the expression and function of ZFAT to activity-inducible T cell apoptosis. It is to be noted herein that the CD4 positive cells were separated from mouse spleen cells using mouse CD4 (L3T4) magnetic beads (Miltenyi Biotec). Further, stimulation of the CD4 positive cells with anti-CD3 antibody and anti-CD28 antibody was carred out by coating a plate with anti-CD3 antibody (145-2C11; BD Pharmingen) (1 ug/ml), washing the plate with PBS(−) and incubating the CD4 positive cells at 37° C. in RPMI-1640 (10% FCS, 50 □M 2-ME) culture medium containing anti-CD28 antibody (37.51; BD Pharmingen) (5 ug/ml). The immunostaining was performed by coating floating cells on a slide glass with CYTOSPIN4 (Thermo) and fixed with 10% formalin. Then, immunostaining was performed using ZFAT-specific antibody (M16) and caspase-9 activation state antibody (Anti-vimentin fragment) (1:200), and the activation of caspase 9 was detected using anti-rat alexa 488 antibody and anti-rabbit alexa 546 antibody (1:200). The nuclear staining was carried out using DAPI (1:200).

Example 15

This example was carried out in the manner similar to that of Example 12 to determine an influence on the number of T cells by the shRNA expression vector formed in Example 2 at the time of stimulation of CD4 positive cells with anti-CD3 antibody and anti-CD28 antibody. After the shRNA expression vector was transducted in CD4 positive cells, it was stimulated with anti-CD3 antibody and anti-CD28 antibody, and an optical microscopic pattern was observed at hour 72 after stimulation. This result indicates that apoptosis can be induced by inhibiting the expression of ZFAT because ZFAT shRNA decreases the number of cells compared to the control (FIG. 14).

INDUSTRIAL APPLICABILITY

The inhibitory RNA for inhibiting the expression of ZFAT gene and the expression vector containing the same according to this invention can inhibit the expression of ZFAT gene and induce apoptosis by introducing them into living bodies such as cells, tissues, individuals, etc., in which their expression is intended to be inhibited. Therefore, the inhibitory RNA for inhibiting the expression of ZFAT gene according to this invention can be used as a medical composition for treatment or prevention of diseases such as cancers and as a molecular target agent or an immunosuppressant having a high selectivity.

The invention claimed is:

1. A cell proliferation inhibiting method, comprising:
expressing in a cell an inhibitory siRNA which comprises a double-stranded siRNA composed of a sense siRNA having a base sequence with contiguous 20 to 30 bases of ZFAT mRNA and an anti-sense siRNA having a base sequence complementary to the base sequence of the sense siRNA to inhibit the expression of ZFAT gene and to inhibit proliferation of the cell; and wherein the double-stranded siRNA is a human ZFAT gene (hZFAT) siRNA comprising a sense siRNA having a base sequence as indicated by SQ ID NO. 3 and an anti-sense siRNA having a base sequence as indicated by SQ ID NO. 4,

```
SQ ID NO. 3:
5'-C CUU AGG CCU CUG AGU ACA CCU GAA-3'

SQ ID NO. 4:
5'-U UCA GGU GUA CUC AGA GGC CUA AGG-3'.
```

2. The cell proliferation inhibiting method as claimed in claim 1, wherein the base sequence of the sense siRNA comprises contiguous 23 to 27 basis of ZFAT mRNA.

3. The cell proliferation inhibiting method as claimed in claim 1, wherein the double-stranded siRNA is a double-stranded siRNA with one to six nucleotides connected to each strand at its 3'-terminus.

4. The cell proliferation inhibiting, method as claimed in claim 1, wherein the inhibitory siRNA for inhibiting the expression of ZFAT gene is a siRNA comprising a sense siRNA having a base sequence of contiguous 20 to 30 bases of ZFAT mRNA and an anti-sense siRNA having a base sequence complementary to the base sequence of the sense siRNA or a shRNA with the sense siRNA and the anti-sense siRNA connected to each other through a loop sequence.

5. The cell proliferation inhibiting, method as claimed in claim 1, wherein the base sequence of the sense siRNA comprises contiguous 23 to 27 bases of ZFAT mRNA.

6. The cell proliferation inhibiting method inhibitory siRNA as claimed in claim 1, wherein the loop sequence forms a hairpin structure comprising a spacer oligonucleotide composed of one to six bases and connecting the sense siRNA to the anti-sense siRNA.

7. A apoptosis induction method, comprising:
expressing in a cell an inhibitory siRNA which comprises a double-stranded siRNA composed of a sense siRNA having a base sequence with contiguous 20 to 30 bases of ZFAT mRNA and an anti-sense siRNA having a base sequence complementary to the base sequence of the sense siRNA to inhibit the expression of ZFAT gene and to induce apoptosis; and wherein the double-stranded siRNA is a human ZFAT gene (hZFAT) siRNA comprising a sense siRNA having a base sequence as indicated by SQ ID NO. 3 and an anti-sense siRNA having a base sequence as indicated by SQ ID NO. 4,

```
SQ ID NO. 3:
5'-C CUU AGG CCU CUG AGU ACA CCU GAA-3'

SQ ID NO. 4:
5'-U UCA GGU GUA CUC AGA GGC CUA AGG-3'.
```

8. The apoptosis induction method as claimed in claim 7, wherein the base sequence of the sense siRNA comprises contiguous 23 to 27 bases of ZFAT mRNA.

9. The apoptosis induction method as claimed in claim 7, wherein the double-stranded siRNA is a double-stranded siRNA having one to six nucleotides added to each strand at its 3'-terminus.

10. The apoptosis induction method as claimed in claim 7, wherein the inhibitory siRNA for inhibiting the expression of ZFAT gene is a siRNA comprising a sense siRNA having a base sequence of contiguous 20 to 30 bases of ZFAT mRNA and an anti-sense siRNA having a base sequence complementary to the base sequence of the sense siRNA or a shRNA with the sense siRNA and the anti-sense siRNA joined to each other through a loop sequence.

11. The apoptosis induction method as claimed in claim 7, wherein the base sequence of the sense siRNA comprises contiguous 23 to 27 bases of ZFAT mRNA.

12. The apoptosis induction method inhibitory siRNA as claimed in claim 7, wherein the loop sequence forms a hairpin structure comprising a spacer oligonucleotide composed of one to six bases and joining the sense siRNA to the anti-sense siRNA.

13. An immune inhibition method, comprising:
expressing in a cell an inhibitory siRNA which comprises a double-stranded siRNA composed of a sense siRNA having a base sequence with contiguous 20 to 30 bases of ZFAT mRNA and an anti-sense siRNA having a base sequence complementary to the base sequence of the sense siRNA or an expression vector to inhibit the expression of ZFAT gene and to inhibit an immune response in a living body; and wherein the double-stranded siRNA is a human ZFAT gene (hZFAT) siRNA comprising a sense siRNA having a base sequence as indicated by SQ ID NO. 3 and an anti-sense siRNA having a base sequence as indicated by SQ ID NO. 4,

```
SQ ID NO. 3:
5'-C CUU AGG CCU CUG AGU ACA CCU GAA-3'

SQ ID NO. 4:
5'-U UCA GGU GUA CUC AGA GGC CUA AGG-3'.
```

14. The immune inhibition method as claimed in claim 13, wherein the base sequence of the sense siRNA comprises 23 to 27 bases of ZFAT.

15. The immune inhibition method as claimed in claim 13, wherein the double-stranded siRNA is a double-stranded siRNA with one to six nucleotides bonded to each strand at its 3'-terminus.

16. The immune inhibition method as claimed in claim 13, wherein the inhibitory siRNA for inhibiting the expression of ZFAT gene is a siRNA comprising a sense siRNA having a base sequence of contiguous 20 to 30 bases of ZFAT mRNA and an anti-sense siRNA having a base sequence complementary to the base sequence of the sense siRNA or a shRNA with the sense siRNA and the anti-sense siRNA joined to each other through a loop sequence.

17. The immune inhibition method as claimed in claim 13, wherein the base sequence of the sense siRNA comprises contiguous 23 to 27 bases of ZFAT mRNA.

18. The immune inhibition method inhibitory siRNA as claimed in claim 13, wherein the loop sequence forms a hairpin structure comprising a spacer oligonucleotide composed of one to six bases and joining the sense siRNA to the anti-sense siRNA.

19. The cell proliferation inhibiting method according to claim 1, wherein said inhibitory siRNA is introduced into said cell in an expression vector.

20. The apoptosis induction method according to claim 7, wherein said inhibitory siRNA is introduced into said cell in an expression vector.

21. The immune inhibition method according to claim 13, wherein said inhibitory siRNA is introduced into said cell in an expression vector.

\* \* \* \* \*